United States Patent [19]

Schilling, Jr. et al.

[11] Patent Number: 4,659,805

[45] Date of Patent: Apr. 21, 1987

[54] RECOMBINANT ALVEOLAR SURFACTANT PROTEIN

[75] Inventors: James W. Schilling, Jr., Palo Alto; Robert T. White, Fremont; Barbara Cordell, San Francisco, all of Calif.

[73] Assignee: California Biotechnology, Inc., Mountain View, Calif.

[21] Appl. No.: 680,358

[22] Filed: Dec. 11, 1984

[51] Int. Cl.$^4$ ..................... C07K 13/00; A61K 37/02
[52] U.S. Cl. ..................................... 530/350; 530/324
[58] Field of Search ................. 260/112.5 R; 530/350, 530/324; 514/21

[56] References Cited

U.S. PATENT DOCUMENTS

| | | | |
|---|---|---|---|
| 4,312,860 | 1/1982 | Clements | 514/78 |
| 4,506,013 | 3/1985 | Hershberger et al. | 435/172.3 |
| 4,562,003 | 12/1985 | Lewicki | 72/38 |

OTHER PUBLICATIONS

Fujiwara, et al., *Lancet* (1980) 1:55.
Hallman, M., et al., *Pediatric Clinics of North America* (1982) 29:1057-1075.
Hallman, M., et al., *Pediatrics* (1983) 71:473-482.
Chem. Abstr., vol. 103, 1985, Abstr. No. 856196b; Balis et al.
Chem. Abstr., vol. 99, 1983, Abstr. No. 155807, Maki.
Chem. Abstr., vol. 102, 1985, 102; 217062f, Whitsett et al.
Biological Abstr., vol. 75, 1982, Abstr. No. 14696, Shelley et al.
Biological Abstr., vol. 80, 1985, Abstr. No. 63225.
Chem. Abstr., vol. 101, 1984, Abstr. No. 2279634, Balis et al.
Chem. Abstr., vol. 91, 1979, Abstr. No. 190210t, Bruni et al.
Chem. Abstr., vol. 102, (1985), 217062.
Biol. Abstr., vol. 75, 14696, (1983).
Biol. Abstr., vol. 80, 63225, (1985).
Chem. Abstr., vol. 99, (1983), 155807.
Chem. Abstr., vol. 101, (1984), 227963.
Chem. Abstr., vol. 103, (1985), 85619.
Chem. Abstr., vol. 91, (1979), 190210.

*Primary Examiner*—Delbert R. Phillips
*Attorney, Agent, or Firm*—Ciotti & Murashige

[57] ABSTRACT

The complete coding sequences and amino acid sequences for both canine and human alveolar surfactant protein (ASP) are disclosed. Methods and vectors for obtaining these proteins in recombinant form are described. The availability of large amounts of these proteins through recombinant techniques permits the use of ASP in suitable pharmaceutical compositions in the treatment of respiratory deficiency syndromes.

14 Claims, 6 Drawing Figures

FIG.1-1

```
TCTGGAGAGT CACTGGACGA AGCC ATG TGG CTG CGC TGT TTG GCC CTC GCC CTC
                              MET Trp Leu Arg Cys Leu Ala Leu Ala Leu
                              -17                                  50
         ─signal sequence─┼─mature ASP sequence─→
ACC TTG CTG ATG GTT TCT GGC ATC GAG AAC ACG AAG GAC GTC TGT GTT GGA
Thr Leu MET Val Ser Gly Ile Glu Asn Thr Lys Asp Val Cys Val Gly
                         -1  +1                 100
                              *
AAC CCT GGC ATC CCT GGC ACT CCT GGG TCC CAT GGC TTG CCA GGC AGA GAT GGG
Asn Pro Gly Ile Pro Gly Thr Pro Gly Ser His Gly Leu Pro Gly Arg Asp Gly
                                                150

AGA GAT GGA GTC AAA GGA GAC CCT GGG CCT CCA GGC CCA GGC TTG GGC CCC GGA
Arg Asp Gly Val Lys Gly Asp Pro Gly Pro Pro Gly Pro Gly Leu Gly Pro Gly
                                        200

GGA ATG CCA GGC CAC CCT GGG CCT AAT GGG ATG ACT GGA GCC CCT GGT GTT GCT
Gly MET Pro Gly His Pro Gly Pro Asn Gly MET Thr Gly Ala Pro Gly Val Ala
                                                        250

GGA GAG CGT GGA GAA AAG GGA GAG CCT GGC GGA AGG GGC CCC CCA GGA CTT CCA
Gly Glu Arg Gly Glu Lys Gly Glu Pro Gly Gly Arg Gly Pro Pro Gly Leu Pro
                                        300

GCT TCT TTA GAT GAA GAG CTC CAA ACC ACA CTC CAC GAC CTC AGA CAT CAA ATC
Ala Ser Leu Asp Glu Glu Leu Gln Thr Thr Leu His Asp Leu Arg His Gln Ile
                 350

CTG CAG ACC ATG GGA GTC CTC AGC TTG CAC GAG TCC CTG CTG GTG GTG GGA AGG
Leu Gln Thr MET Gly Val Leu Ser Leu His Glu Ser Leu Leu Val Val Gly Arg
                 400
```

FIG.1-2

```
                                           450
AAG GTC TTC TCC AGC AAT GGG CAG TCC ATT AAT TTC AAC GAC ATT CAA GAG TTA
Lys Val Phe Ser Ser Asn Gly Gln Ser Ile Asn Phe Asn Asp Ile Gln Glu Leu
                    500
TGT GCC GGG GCA GGC GGC CAA ATT GCT GCC CCG ATG AGC CCA GAA GAG AAT GAA
Cys Ala Gly Ala Gly Gly Gln Ile Ala Ala Pro MET Ser Pro Glu Glu Asn Glu
                         550
GCC GTT GCA AGC ATT GTG AAG AAG TAT AAC ACT TAC GCC TAC CTG GGC CTG GTG
Ala Val Ala Ser Ile Val Lys Lys Tyr Asn Thr Tyr Ala Tyr Leu Gly Leu Val
            600
GAG AGC CCC GAC TCT GGA GAC TTC CAG TAC ATG GAT GGG GCC CCT GTG AAT TAC
Glu Ser Pro Asp Ser Gly Asp Phe Gln Tyr MET Asp Gly Ala Pro Val Asn Tyr
                                                                       *
650
ACC AAC TGG TAC CCC GGG GAG CCC AGA GGT CGG GGC AAA GAG CAG TGT GTG GAG
Thr Asn Trp Tyr Pro Gly Glu Pro Arg Gly Arg Gly Lys Glu Gln Cys Val Glu
                                                              750
ATG TAC ACA GAT GGG CAG TGG AAT AAC AAA AAC TGC CTG CAG TAC CGA CTG GCC
MET Tyr Thr Asp Gly Gln Trp Asn Asn Lys Asn Cys Leu Gln Tyr Arg Leu Ala
                                        800
ATC TGT GAG TTT TGA GCAGCCTCT AAGGCCACAG TAGAGATAGG CCCTGCCTTG CTTTCAGC
Ile Cys Glu Phe End
            231

CT CCATCCTGCAG
```

BamHI
ggatcctcca gcctgagtgc tcttggggaa acatgctgtg taaacactat gcccattttcc tgcctggagc acaggttttg tggtagggct ctcaggggtg aggaggaagc ctggcagccc
                                          50                                         100
ccacatctat aaatgctgcg tctaccttac cctctgactt ggaggcagag ACCCAAGCAG CTGCAGGCTC TGTGTGTGG gtgagtttagc cccatcccct aggttctc cagcttgagg
         150                             200                             300                                                     350
atcgcaggca gagaggacca gcccagcagc cacaggcctg accaaagccc aggctgggaa ggagggcaac tcccatttt ccactggag gtgtttcaca gcacagtcaa cataggtgac
                          400                                            450
ctgcaaagat cctccatgtt gttattttct ttggccagat ccatcctaca ggttcagca gggcctacag gaggggcagt gagagaacag accccaaaaa gaaaggggac tccatgactg
         500                                            550                                                            600
accaccttga gggggccag gctgccgggc cccgttcatc ttttttcatt ctcaggtcgc tgattcttg gagcctgaaa agaaagtaac acagcaggga tgaggacaga tggtgtgagt
                          650                                                            700
cagtgagtga gtgacctgac taatagcctg ggaggacag ggcaggtttt ctgcagagc acggaagatt cagctgaagt caggagggtg aagccagttt cccaggtaa catagtgagg
                       750                                         800
cactgaaaga aaggagacts cactggagcc caggtcccag ggctcccag agctccttac tcttcctcct cctcagcagc ctggagaccc cacaaacctc agccggaggc ctgaagcatg
                       850                                    900                                                            950
aggccatgcc aggtgccagg tgatgctggg aatttcccag ggagcttcgg gtcttcccag cactctggtc gtcgccgcc ctgcctcgtc gggctctgcc cagcttcctg agtcctgaca

FIG. 3-1 gagcacagtg ggggagatgt tggcagagggt ggcagatggg ctcacggcca tcccctcctgcag GAGCAGCCG ACTGACCCA GAGCC    ATG TGG CTG TGC CCT CTG GCC CTC AAC
                                                          ←— signal sequence —||— mature ASP sequence —→    MET Trp Leu Cys Pro Leu Ala Leu Asn
                                                                                                              1050                    1150  BamHI
CTC ATC TTG ATG GCA GCC TCT GGT GCT GTG TGC GAA GTG AAG GAC GTT TGT GTT  GGA AGC CCT GGT ATC CCC GGC ATC CCT GGA TCC CAC GGC CTG CCA
Leu Ile Leu MET Ala Ala Ser Gly Ala Val Cys Glu Val Lys Asp Val Cys Val  Gly Ser Pro Gly Ile Pro Gly Ile Pro Gly Ser His Gly Leu Pro
 *                        1200                                                                  1250
GCC AGG CAC GGG AGA GAT GGT GTC AAA GGA GAC CTC GGC CCT CCA G gta ctgtgctgca gaccccaccc tcagctgagg acacagaccc ctttcagga ggcccatctg
Gly Arg His Gly Arg Asp Gly Val Lys Gly Asp Leu Gly Pro Pro G
 1300                                                                                                                          1400
tccaggcccc taggctgtgg gccatagtga gctgggggct atagtaagct gggtggggact tcagtctgca gggctggtgg gttccctggg ccctatgat ggcgcatcct ggagagtctg
                                                 1350
tccctcatagt gcccacggac tgatagagtg atagctgagc cagcccctggt gataatgggc atcgagtcctc actagcttca accagttgtg ggtgacagat cctacacatc catgtctctt
                                                                                                     1500
         Exon II                                                  1550                                                  1600
ttctctgcag GC CCC ATG GGT CCA CCT GGA GAA ATG CCA TCT CCT CCT GGA AAT GAT GGC CTG CCT GGA GCC CTG CCT GGA GAG TGT GGA GAG
           ly Pro MET Gly Pro Pro Gly Glu MET Pro Cys Pro Pro Gly Asn Asp Gly Leu Pro Gly Ala Pro Gly Ile Pro Gly Glu Cys Gly Glu
                                                                    1650                                  1700
AAG GGC GAG CCT GGC GAC AGG GGC CCT CCA G gtgagcaggg tggggcaggt ggcagtgga aacatgggca caggcaccct gaagtcagtt acacggggat gatggggatc
Lys Gly Glu Pro Gly Arg Gly Arg Gly Pro Pro G

FIG. 3-2

```
                                                                    1750                                                                                    1800              1850
agacaaaccc tacaggttcc ccaagggcat ttggctcaac ctaagtaaga gaggataagc ttgagggaga aagctgaggt gtctggggag tgtggtcaca attcagggaa aggcaggtgt
                                                                                                      1900                                                                          1950
gggaagtcct ccgtgcctca tgaccaccga tgggacacac ctgagtcagg tgtggatga gggacagcac tgggaggcag gggaggcatg tcctgggatg gaggccctgg ggctgtctga
                         2000                                                                                              2050
agggtgaatg cggacgaggc atccagaagc acggtgtgat caggagcccc acagacagag gggaactttg aagctcagag cggtaagcaa gtccatcagg gcagtgcaga gagcatcatg
              2100                                                                                                2150                                               2200
cttgcccttc ggtcggaggg tgcgggagag ggacttgccc cacagaggcg ggcagacaga accccctcgag gacaagagca ggaaagagga caagggggtgg gggtctcagc aggggcaagg
                                                                                                                              2300
cttcactaaa gaataggggga ccacggggtct gagacacact ggaatcttgt tgcccctcct tctgtgtggg gcactctcca cag GG CTT CCA GCT CAT CTA GAT GAG CTC CAA GCC ACA
                         2350                                                                      2400       Exon III       ly Leu Pro Ala His Leu Asp Glu Leu Gln Ala Thr
caaaacacct cgtggcagca agtgggagtc ttcactggcc tgccccctcct tctgtgtggg gcactctcca cag                                                                                      2550
2450
CTC CAC GAC TTT AGA CAT CAA ATC CTG CAG ACA AGG GGA G gtaaggggga ccccctgggc tcacggggta ggagtttccc acaaattccc ctcattctca gcaccagctt
Leu His Asp Phe Arg His Gln Ile Leu Gln Thr Arg Gly A
```

FIG. 3-3

```
                                                                                            2650
ctagaacata gagattacaa ataggcatgc acatgcaggt cttggggaaa ggaattgacg cttgcttttc ttgatgtctt ttgaatggcc cagaggagac agaagcagac acaattcact
                            2700                    EcoRI               2750
tccccgattt cataggaaag caagttctct atctgccttg ctttccactg aattcacagg aaattgcacc atttctggca ataagtaatt gttacttagg tgaatgaata aatggaggag
     2800                                                      2850                                                   2900
agtctaaaag tgaatttaga aaactgcaat tggaagagga agagaagaca cagagagagg cagagatgga gagagagacc gagactgggg agaatctggt agcagagacc ccaggtgagg gaggtggctt
                                       2950    Exon IV                                                   3000
agagacaaag tggtcagtgg cctgacccgg actccctgc tctcag    CC CTC AGT CTG CAG GGC TCC ATA ATG ACA GTA GGA GAG AAG GTC TTC TCC AGC AAT GGG
                                                  1a Leu Ser Leu Gln Gly Ser Ile MET Thr Val Gly Glu Lys Val Phe Ser Ser Asn Gly
                                  3050                                                                         3100
CAG TCC ATC ACT TTT GAT GCC ATT CAG GAG GCA TGT GCC AGA GCA GGC GGC ATT GCT GTC CCA AGG AAT CCA GAG AAT CAG GCC ATT GCA
Gln Ser Ile Thr Phe Asp Ala Ile Gln Glu Ala Cys Ala Arg Ala Gly Gly Ile Ala Val Pro Arg Asn Pro Glu Asn Gln Ala Ile Ala
 HindIII                                     3150                                                                  3200
AGC TTC GTG AAG AAG TAC AAC ACA TAT GCC TAT GTA GGC CTG ACT GAG GGT CCC AGC CCT GGA GAC TTC CGC TAC TCA GAC GGG ACC CCT GTA AAC
Ser Phe Val Lys Lys Tyr Asn Thr Tyr Ala Tyr Val Gly Leu Thr Glu Gly Pro Ser Pro Gly Asp Phe Arg Tyr Ser Asp Gly Thr Pro Val Asn
```

FIG. 3-4

```
                                                        3250                                                                3300
TAC ACC AAC TGG TAC CGA GGG GAG CCC GCA GGT CGG GGA AAA GAG CAG TGT CTG GAG ATG TAC AGA GAT GGG CAG TGG AAT GAC AGG AAC TGC CTG
Tyr Thr Asn Trp Tyr Arg Gly Glu Pro Ala Gly Arg Gly Lys Glu Gln Cys Val Glu MET Tyr Arg Asp Gly Gln Trp Asn Asp Arg Asn Cys Leu
                                                                3350                                                        3400
TAC TCC CGA CTG ACC ATC TGT GAG TTC TGA       GAGGCAT TTAGGCCATG GGACAGGGAG GACGCTCTCC TTGTCGGCCT CCATCCTGAG GCTCCACTTG GTCTGTGAGA
Tyr Ser Arg Leu Thr Ile Cys Glu Phe
             EcoRI    3450                                      3500                                                        3650
TGCTAGAACT CCCTTTCAAC AGAATTCCAC TTGTGGCTAT TGGGACTGGA GGCACCCTTA GCCACTTCAT TCCTCTGATG GCCCTGACT CTTCCCCATA ATCACTTCCAC CAGCCTTGAC
      3550                                            3600                                                                  3650
ACTCCCCTTG CAAACTCTCC CAGCCACTGCA CAGCCACTGCA CCCCCAGGCAG CCACTCTTAG CCTTGGCCT CGACATGAGA TGCAGCCCTC CTTATTCCCC ATCTGGTCCA GTTCCTTCAC TTACAGATGG
                                                                                    3750
CAGGCAGTGAG GTCTTGGGGT AGAAGGACCC TCCAAAGTCA CACAAAGTGC CTGCCTCCTG CTCTCTCTCT GCAACCCAGT GCCATCAGGA TGAGGAATCC TGGCCAAGCA
      3800                                                                3850
TAATGACAGA GAGAGGCAGA CTTCGGGGAA GCCCTGACTG TCCAGAGCTA AGGACACAGT GGAGATTCTC TGGCACTCTG AGTCTCTCT GGCAGGCCTG CTCAGGCTCT CCATGAGGTT
```

FIG. 3-5

```
                                                                                                              4000
     3900                                        3950
AGAAGGCCAG GTAGTTGTTC CAGCAGGGTG GTGGCCAAGC CAACCCCATG ATTGATGTGT ACGATTCACT CCTTTGAGTC TTTGAATGGC AACTCAGCCC CCTGACCTGA AGACAGCCAG
             4050                                                     4100
CCTAGCCCTC TAGGTGACCT AGAGCCGCCT TCAGATCTGA CCCGAGTAAC TTTCAACTGA TGAACAAATC TGCACCCTAC TTCAGATTTC AGTGGGCATT CACATCACCC CCACACCACT
                                   4150                                            4200                                          4250
GGCTCTCGCTT TCTCCTTTCA TTAATCCATT CACCCAGATA TTTCATTAAA ATTATCACCT GCCAGGTCTT AGGATATGTC GTGGGGTGGG CAAGGTAATC AGTGACAGTT GAAGATTTTT
                                                4300                                                  4350
TTTTCCCAGA GCTTATGTCT TCATCTGTGA AATGGGAATA AGATACTTGT TGCTGTCACA GTTATTACCA TCCCCCCAGC TACCAAAATT ACTACCAGAA CTGTTACTAT ACACAGAGCC
                      4400                                                4450
TATTGACTGA GCACTATCA TTTGCCAAGA ACCTTGACAA GCACTTCTAA TACAGCATAT TATTCCAGAG TATGTACTAT TCAATCTTCA CACAATGTCA CGGGACCAGT ATTGTTTCCT CATTTTTTAT
           4500 HindIII                                 4550                 BamHI                                         4600
AAGGACACTG AAGCTTGGAG GAGTTAAATG TTTTGAGTAT TATTCCAGAG ACCAAGTGGC AGAGGCTGGA TCCAAACCCA TCTTCCTGGA CCTGAAGCTT  HindIII  ATGCTTCCAG CCTCCCACTC
                       HindIII                   4650                                               4700
CTGAGCTCAA TAAAGATGAT TTAAGCTtaa taaatcgtga atgtgttcac atgagtttcc atagctttgg ttccaagaaa tatcacattt ctgtatttt gtaaatcaaa tgaactctga
     4750                                            HindIII
ctctgagccc cacttgcctg aagattggaa attcaatctc aggatgtg ... (1100 bp) ... aagctt
```

FIG. 3-6

Bam BstEII Hinf Bam      RI   RI   BstEII   Bam
gHS
gHS(BstEII)
gHS(HinfI)
gHS(HinfI/RI)
+
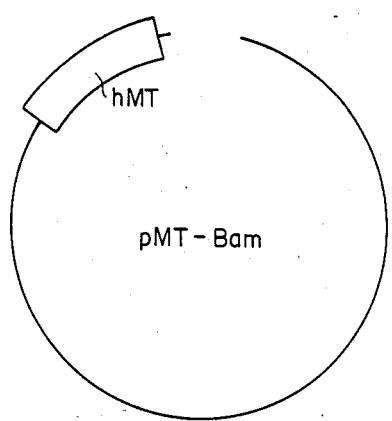
pMT-Bam
OR
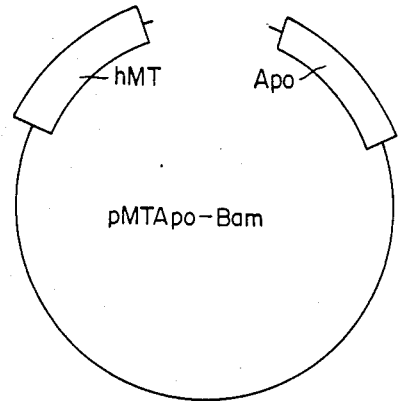
pMTApo-Bam
FIG. 4A

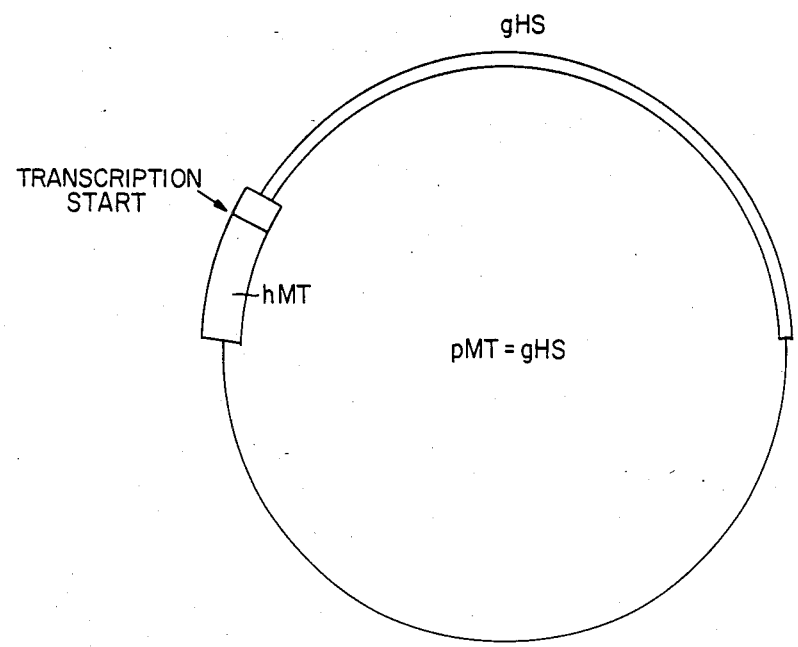
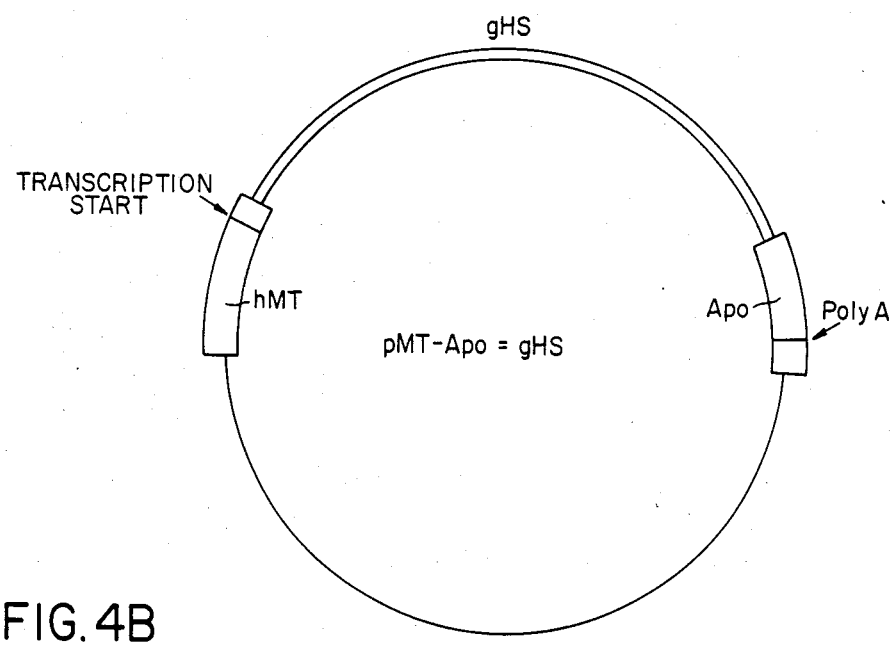
FIG. 4B

```
                                                                                                                    500
                                   ATGACAGTAGGAGAGAAGTCTTCTCCAGCAATGGGCAGTCCATCACTTTTGATGCC
                                   METThrValGlyGluLysValPheSerSerAsnGlyGlnSerIleThrPheAspAla
                                                        550
ATTCAGGAGGCCATGTGCCAGAGCAGGCCGCCGCATTGCTGTCTCCAAGGAATCCAGAGGAAAATGAGGCCATTGCAAGCTTCGTGAAGAAG
IleGlnGluAlaCysAlaArgAlaGlyArgIleAlaValProArgAsnProGluGluAsnGluAlaIleAlaSerPheValLysLys
             600                                           650
TACAACACATATGCCTATGTAGGCCTGACTGAGGGTCCCAGCCCTGACTTCCGTACTCAGACGGACCCCTGTAAACTACACCAAC
TyrAsnThrTyrAlaTyrValGlyLeuThrGluGlyProSerProAspPheArgTyrSerAspGlyThrProValAsnTyrThrAsn
                        700                                          750
TGGTACCGAGGGGAGCCCCGCAGGTCGGGAAAAGAGCAGTGTGTGGAGATGTACACAGATGGCCAGTCGAATGACAGGAACTGCCTGTAC
TrpTyrArgGlyGluProAlaGlyArgGlyLysGluLysGlyLysValGluMETTyrThrAspGlyGlnTrpAsnAspArgAsnCysLeuTyr
                                  800                                          850
TCCCGACTGACCATCGTGAGTTCTGAGAGGCATTAGCCAATGGGACAGGGAGGACGCTCCTCCTTGTCCGCCTCCATCCTGAGGCTCCA
SerArgLeuThrIleCysGluPhe
                                             900                                          950
CTTGGTCTGTGAGATGCTAGAACTCCCTTTCAACAGAATTCCACTTGTGGCTATTGGGACTGGAGGCACCCTTAGCCACTTCATTCCTCT
                                                       1000
GATGGGCCCTGACCCTTCCCATAATCACTGACCAGCCTTGACACTCCCCTTGCAAACTCT
```

FIG. 5

RECOMBINANT ALVEOLAR SURFACTANT PROTEIN

TECHNICAL FIELD

The invention relates to the field of recombinant protein production. More specifically it relates to the production of alveolar surfactant protein (ASP) which is useful in the management of certain respiratory diseases.

BACKGROUND ART

The human lung is composed of a large number of small sacs or alveoli in which gases are exchanged between the blood and the air spaces of the lung. In healthy individuals, this exchange is mediated by the presence of a protein containing surfactant complex which is synthesized in the microsomal membranes of type II alveolar cells. In the absence of adequate levels of this complex, a lung cannot properly function—i.e., the alveoli collapse during exhalation, and cannot be subsequently re-inflated by inhaling. Thus, the untreated inability to synthesize this complex may result in death or in severe physical damage.

The best documented instance of inadequate surfactant complex levels occurs in premature infants and infants born after complicated pregancies, and is widely known as respiratory distress syndrome (RDS). A widely publicized form of this syndrome has been designated hyaline membrane disease, or idiopathic RDS. RDS is currently the leading cause of infant mortality and morbidity in the United States and in other developed countries, and substantial efforts have been directed to diagnosis and treatment. Current treatment has focused on mechanical (pressure) ventilation which, at best, is an invasive stop-gap measure that often results in damage to the lung and other deleterious side effects, including complications such as bronchopulmonary dysplasia, interstitial emphysema and pneumothorax. Mental retardation has also resulted on occasion when this treatment was used (Hallman, M., et al, *Pediatric Clinics of North America* (1982) 29: 1057–1075).

Limited attempts have been made to treat the syndrome by surfactant substitution. This would be a method of choice, as, in general, only one administration is required, and the potential for damage is reduced. For example, Fujiwara, et al, *Lancet* (1980) 1: 55-used a protein-depleted surfactant preparation derived from bovine lungs; the preparation is effective but immunogenic. Hallman, M., et al, *Pediatrics* (1983) 71: 473–482 used a surfactant isolate from human amniotic fluid to treat a limited number of infants with some success. U.S. Pat. No. 4,312,860 to Clements discloses an artificial surfactant which contains no protein and is said to be useful in this approach although no data are shown. In short, surfactant substitution has not been widely used clinically.

The preferred surfactant substitute would be the lung surfactant complex itself. This complex is composed of apoprotein, two major phospholipids (dipalmitoyl phosphocholine (DPPC) and phosphatidylglycerol (PG) and calcium ions. The apoprotein contains proteins having molecular weights of about 32,000 daltons and of about 10,000 daltons. The 32,000 dalton protein is glycosylated and contains hydroxyproline.

A major reason for the limited progress in surfactant replacement therapy has been the lack of availability of the protein portion of the complex. Replacement therapies have focused on attempts to use the lipid components alone, and it appears that the performance of such treatment can be markedly improved by addition of the apoprotein (Hallman, M., et al, *Pediatric Clinics of North America* (1982) (supra)). At present, however, these proteins are available only from normal adult human lung, and from amniotic fluid. Even efficient isolation procedures would not provide an adequate supply. Thus, it would be desirable to have available a method for producing practical quantities of apoprotein for use alone or in conjunction with the saturated phospholipid portion of the complex.

DISCLOSURE OF INVENTION

The invention provides a means for obtaining the aproprotein portion of the lung surfactant complex in quantity and under conditions which permit optimization of its features. The remaining components of the complex, dipalmitoyl phosphocholine and phosphotidylglycerol, along with calcium ions are already readily available. The availability of required quantities of manipulable apoprotein both makes possible research efforts to optimize the form of complex useable in therapy, and opens the possibility for routine replacement therapy of respiratory distress syndrome.

Thus, in one aspect, the invention relates to recombinantly produced human or canine alveolar surfactant protein (ASP). These proteins have amino acid sequences substantially similar to those shown in FIGS. 1 and 3. The invention further relates to a genomic DNA sequence encoding human ASP and to intronless DNA sequences encoding human and canine ASP, to expression vectors suitable for production of these proteins, to recombinant hose cells transformed with these vectors, and to methods for producing the recombinant ASPs and their precursors. In other aspects the invention relates to pharmaceutical compositions containing human ASP and to methods of treating RDS using them.

BRIEF DESCRIPTION OF THE DRAWINGS

FIG. 1 shows the DNA sequence encoding canine ASP, along with the deduced amino acid sequence.

FIG. 3 shows the nucleotide sequence of the human ASP gene and the deduced amino acid sequence.

FIG. 4 shows the construction of the expression vector pMT:gHS derivatives.

FIG. 5 shows the sequence of the 3' terminal portion of human ASP cDNA.

FIG. 6 is an autoradiograph of S-Met-labeled, secreted proteins from CHO cells transfected with λ:gHS-15.

MODES OF CARRYING OUT THE INVENTION

A. Definitions

Figure 2:
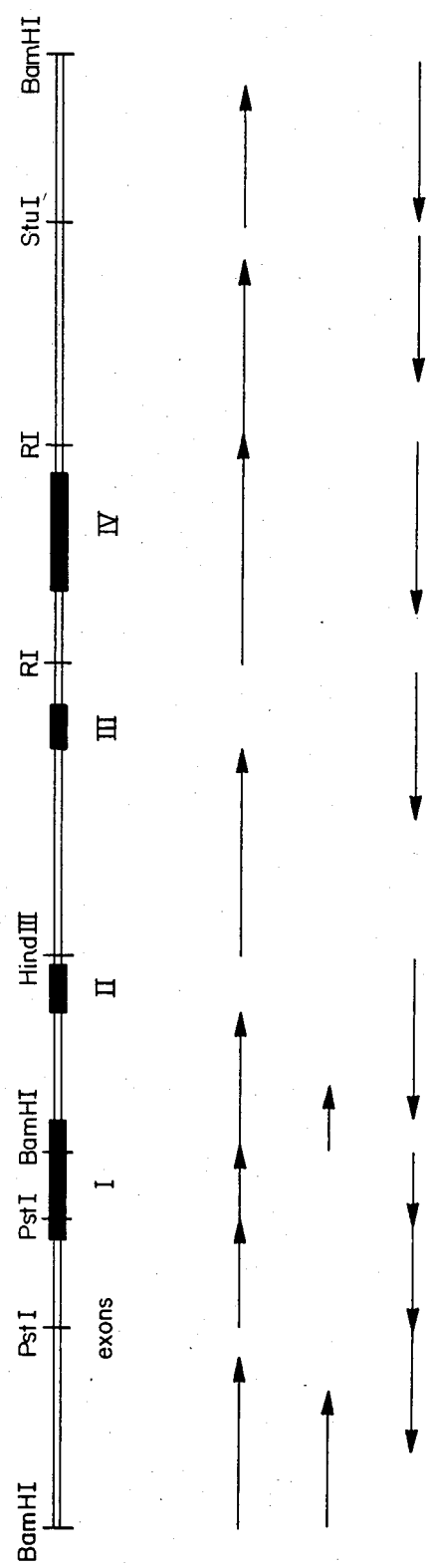
FIG. 2 shows the sequencing strategy for the two BamHI fragments constituting the human ASP gene.

As used herein, "alveolar surfactant protein (ASP)" refers to the apoprotein associated with the lung surfactant complex. Human ASP has the amino acid sequence shown in FIG. 3; ASP proteins derived from other species such as dogs, monkeys, or other mammals have substantial degrees of homology with this sequence (see FIG. 1 in connection with the canine ASP). The human ASP recombinant protein of this invention has an amino acid sequence substantially similar to that shown in FIG. 3, but minor modifications of this sequence which do not destroy activity also fall within the definition and within the protein of the invention, as further set forth below. Also included within the definition are fragments of the entire sequence which retain activity.

As is the case for all proteins, ASP can occur in neutral form or in the form of basic or acid addition salts depending on its mode of preparation, or, if in solution, upon its environment. It is well understood that proteins in general, and, therefore, ASP, in particular, may be found in the form of its acid addition salts involving the free amino groups, or basic salts formed with free carboxyls. Pharmaceutically acceptable salts may, indeed, enhance the functionality of the protein. Suitable pharmaceutically acceptable acid addition salts include those formed from inorganic acids such as, for example, hydrochloric or sulfuric acids, or from organic acids such as acetic or glycolic acid. Pharmaceutically acceptable bases include the alkali hydroxides such as potassium or sodium hydroxides, or such organic bases as piperidine, glucosamine, trimethylamine, choline, or caffeine. In addition, the protein may be modified by combination with other biological materials such as lipids and saccharides, or by side chain modification, such as acetylation of amino groups, phosphorylation of hydroxyl side chains, or oxidation of sulfhydryl groups or other modification of the encoded primary sequence. Indeed, in its native form, ASP is a glycosylated protein, and certain of the encoded proline residues have been converted to hydroxyproline. It is also found in association with the phospholipds DPPC and PG. Included within the definition of ASP herein are glycosylated and unglycosylated forms, hydroxylated and non-hydroxylated forms, the apoprotein alone, or in association with lipids, and, in short, any composition of an amino acid sequence substantially similar to that shown in FIG. 1 or 3 which retains its ability to facilitate the exchange of gases between the blood and lung air spaces and to permit re-inflation of the alveoli.

It is further understood that minor modifications of primary amino acid sequence may result in proteins which have substantially equivalent or enhanced activity as compared to the sequence set forth in FIG. 1 or 3. These modifications may be deliberate, as through site-directed mutagenesis, or may be accidental, such as through mutation of hosts which are ASP producing organisms. All of these modifications are included as long as the ASP activity is retained.

"ASP activity" is defined as activity in the in vivo assay of Robertson, B. *Lung* (1980) 158: 57–68. In this assay, the sample to be assessed is administered through an endotrachial tube to fetal rabbits or lambs delivered prematurely by Caesarian section. (These "preemies" lack their own ASP, and are supported on a ventilator.) Measurements of lung compliance, blood gases and ventilator pressure provide indices of activity. Preliminary assessment of surfactant function may also be made by an in vitro assay, for example that of King, R. J., et al, *Am J Physiol* (1972) 223: 715–726, which utilizes a straightforward measurement of surface tension at a air-water interface.

"Operably linked" refers to a juxtaposition wherein the components are configured so as to perform their usual function. Thus, control sequences operably linked to coding sequences are capable of effecting the expression of the coding sequence.

"Control sequence" refers to a DNA sequence or sequences which are capable, when properly ligated to a desired coding sequence, of effecting its expression in hosts compatible with such sequences. Such control sequences include promoters in both procaryotic and eucaryotic hosts, and in procaryotic organisms also include ribosome binding site sequences, and, in eucaryotes, termination signals. Additional factors necessary or helpful in effecting expression may subsequently be identified. As used herein, "control sequences" simply refers to whatever DNA sequence may be required to effect expression in the particular host used.

"Cells" or "recombinant host cells" or "host cells" are often used interchangably as will be clear from the context. These terms include the immediate subject cell, and, of course, the progeny thereof. It is understood that not all progeny are exactly identical to the parental cell, due to chance mutations or differences in environment. However, such altered progency are included when the above terms are used.

B. General Description

The methods illustrated below to obtain an intronless DNA sequence encoding human ASP are merely for purposes of illustration and are typical of those that might be used. However, other procedures may also be employed, as is understood in the art.

B.1. The Nature of the Surfactant Complex

The alveolar surface of lung has been studied extensively by a number of techniques, and by a number of groups. It appears that the basement membrane of the alveolous is composed of type I and type II alveolar cells, of which the type II cells comprise approximately 3% of the surface. The type II cells are responsible for the exocrine secretion of materials into a lining fluid layer covering the basement membrane, which materials decrease the surface tension between the liquid of the lining and the gas phase of the contained volume. The fluid layer, then, is comprised of water derived from the blood plasma of the alveolar capillaries, and the surfactant secretions of the type II cells.

The type II cells, themselves, contain 60–100 pg of protein and about 1 pg of lipid phosphorus per cell where the ratio between type II cell DPPC and PG phosphorus is about 8 to 1. Studies of the apoprotein components have been based on pulmonary lavage from various species, and have been shown to comprise two major proteins, apoprotein "A" of molecular weight approximately 10,000, and apoprotein "B" with a molecular weight of about 34,000–35,000. (Kikkawa, Y., et al, *Laboratory Investigation* (1983) 49: 122–139.) It is not clear whether the apoproteins are bound to the phospholipid component (King, R. J., et al, *Am Rev Respir Dis* (1974) 110: 273) or are not (Shelly, S. A., et al, *J Lipid Res* (1975) 16: 224).

It has been shown that the higher molecular weight protein obtained by pulmonary lavage of dogs, and separated by gel electrophoresis is composed of 3 major components of molecular weight 29,000, 32,000, and 36,000 daltons. (See, U.S. Ser. No. 665,018, filed Oct. 26, 1984, assigned to the same assignee, and incorporated herein by reference.) The 32,000 dalton protein was used to obtain sequence data, as set forth below; however, all 3 of these proteins have identical N-terminal sequences, and there is evidence that they differ only in degree of glycosylation. Digestion of the 36 kD and 32 kD bands with endoglycosidase F, which removes carbohydrate side chains, results in products which co-migrate with the 29 kD component. The mobility of the 29 kD component is unaffected by this treatment. It has also been shown that the 32 kD fraction aggregates into dimers and trimers.

B.2. Cloning of Coding Sequences for Canine and Human ASP

The entire canine and human ASP encoding sequences have been cloned, and are available for expression in a variety of host cells as set forth in ¶ C below.

The canine sequence was obtained from a cDNA library prepared from mRNA isolated from adult canine lung, by probing with two sets of synthetic oligonucleotides, one prepared to accommodate all the possible sequences encoding amino acids 1-5 of the N-terminal sequence and the other amino acids 7-11 of that sequence, as well as a single 15-mer encoding the amino acids 1-5, selected on the basis of mammalian codon preference. Immobilized cDNA from the library constructed in *E. coli* was probed using these oligonucleotide sets. False positives were minimized by requiring hybridization to more than one set. Successfully hybridizing clones were sequenced, and one was shown to contain the correct N-terminal sequence.

The cDNA insert from the successful clone, excised with PstI, was then used as a probe of the original canine cDNA library, to obtain two additional clones containing inserts encoding other regions of the ASP which, together with this probe, span 844 nucleotides containing the complete coding sequence of canine 32 kD ASP. The entire nucleotide sequence of the three appropriate inserts, and the deduced 256 amino acid sequence are shown in FIG. 1.

This same originally retrieved N-terminal encoding fragment used above was also used as a probe to obtain fragments from a human genomic library in λ phage Charon 28. The entire coding sequence for human ASP was found to be contained in a single phage plaque, and to be contained within 2 contiguous BamHI fragments, a 5' 1.2 kb and a 3' 3.5 kb fragment. The pertinent portions of these fragments, encoding human ASP, and containing 3 introns, are shown in FIG. 3; the deduced amino acid sequence of human ASP, contains 228 amino acids, and is preceded by a signal sequence of at least 25 amino acids.

Extensive homology exists between the canine and human amino acid sequences.

B.3. Expression of Human ASP

As the complete nucleotide sequences encoding human and canine ASP are now available, these may be expressed in a variety of systems as set forth in ¶ C. If procaryotic systems are used, an intronless coding sequence should be used, along with suitable control sequences. The cDNA of the canine ASP may be excised with suitable restriction enzymes and ligated into procaryotic vectors for such expression. For procaryotic expression of human ASP, the two BamHI genomic fragments containing the two introns should be modified to remove these introns, either by site-directed mutagenesis, or by retrieving corresponding portions of cDNA and substituting them for the intron-containing genomic sequences. The intronless coding DNA is then ligated into expression vectors for procaryotic expression.

In the example below, the human sequence is used directly in an expression system capable of processing the introns, a mammalian host cell culture. To effect such expression, the two BamHI sequences are ligated downstream from a controllable mammalian promoter which regulates the expression of these sequences in CHO cells.

B.4. Protein Recovery

The ASP protein may be produced either as a mature protein or a fusion protein, or may be produced along with a signal sequence in cells capable of processing this sequence for secretion. It is advantageous to obtain secretion of the protein, as this minimizes the difficulties in purification; thus it is preferred to express the human ASP gene which includes the codons for native signal sequence in cells capable of appropriate processing. It has been shown that cultured mammalian cells are able to cleave and process heterologous mammalian proteins containing signal sequences, and to secrete them into the medium (McCormick, F., et al, *Mol Cell Biol* (1984) 4: 166).

When secreted into the medium, the ASP protein is recovered using standard protein purification techniques. The purification process is simplified, because relatively few proteins are secreted into the medium, and the majority of the secreted protein will, therefore, already be ASP. However, while the procedures are more laborius, it is within the means known in the art to purify this protein from sonicates or lysates of cells in which it is produced intracellularly in fused or mature form.

B.5. Administration and Use

The purified protein can then be used in pharmaceutical compositions appropriate for administration for the treatment of respiratory distress syndrome in infants or adults. The compositions and protein products of the invention are also useful in treating related respiratory diseases such as pneumonia, emphysema and bronchitis. For use in such treatment, the ASP is combined with natural or synthetic lipids to reconstruct a surfactant complex. The complex contains about 50% to almost 100% (wt/wt) lipid and 50% to less than 1% ASP; preferably ASP is 5%-20% of the complex. The lipid portion is preferably 80%-90% (wt/wt) DPPC with the remainder unsaturated phosphatidyl choline, phosphatidyl glycerol, triacylgylcerols, palmitic acid or mixtures thereof. The complex is reassembled by mixing a solution of ASP with a suspension of lipid lipsomes, or by mixing the lipid protein solutions directly in the presence of detergent or an organic solvent. The detergent or solvent may then be removed by dialysis.

The compositions containing the complex are preferably those suitable for endotracheal administration, i.e., generally as a liquid suspension, as a dry powder "dust" or as an aerosol. For direct endotracheal administration, the ASP is suspended in a liquid with suitable excipients such as, for example, water, saline, dextrose, or glycerol and the like. The compositions may also contain small amounts of non-toxic auxiliary substances such as pH buffering agents, for example, sodium acetate or phosphate. To prepare the "dust", the complex, optionally admixed as above, is lyophilized, and recovered as a dry powder.

If to be used in aerosol administration, the ASP is supplied in finely divided form along with an additional surfactant and propellent. Typical surfactants which may be administered are fatty acids and esters, however, it is preferred, in the present case, to utilize the other components of the surfactant complex, DPPC and PG. Useful propellents are typically gases at ambient conditions, and are condensed under pressure.

Lower alkanes and fluorinated alkanes, such as Freon, may be used. The aerosol is packaged in a container equipped with a suitable valve so that the ingredients may be maintained under pressure until released.

The human ASP along with other components of the surfactant complex are administered, as appropriate to the dosage form, by endotracheal tube, by aerosol administration, or by nebulization of the suspension or dust into the inspired gas. Amounts of human ASP between about 0.1 mg and 10 mg are administered in one dose. For use in newly born infants, one administration is generally sufficient. For adults, sufficient reconstituted complex is administered to replace demonstrated levels of deficiency (Hallman, M., et al, *J Clinical Investigation* (1982) 70: 673–682).

C. Standard Methods

Most of the techniques which are used to transform cells, construct vectors, extract messenger RNA, prepare cDNA libraries, and the like are widely practiced in the art, and most practitioners are familiar with the standard resource materials which describe specific conditions and procedures. However, for convenience, the following paragraphs may serve as a guideline.

C.1. Hosts and Control Sequences

Both procaryotic and eucaryotic systems may be used to express the ASP encoding sequences; procaryotic hosts are the most convenient for cloning procedures. Procaryotes most frequently are represented by various strains of *E. coli;* however, other microbial strains may also be used. Plasmid vectors which contain replication sites and control sequences derived from a species compatible with the host are used; for example, *E. coli* is typically transformed using derivatives of pBR322, a plasmic derived from an *E. coli* species by Bolivar, et al, *Gene* (1977) 2: 95. pBR322 contains genes for ampicillin and tetracycline resistance, and thus provides additional markers which can be either retained or destroyed in constructing the desired vector. Commonly used procaryotic control sequences which are defined herein to include promoters for transcription initiation, optionally with an operator, along with ribosome binding site sequences, include such commonly used promoters as the beta-lactamase (penicillinase) and lactose (lac) promoter systems (Chang, et al, *Nature* (1977) 198: 1056 and the tryptophan (trp) promoter system (Goeddel, et al *Nucleic Acids Res* (1980) 8: 4057 and the lambda derived $P_L$ promoter and N-gene ribosome binding site (Shimatake, et al, *Nature* (1981) 292: 128).

In addition to bacteria, eucaryotic microbes, such as yeast, may also be used as hosts. Laboratory strains of *Saccharomyces cerevisiae,* Baker's yeast, are most used although a number of other strains are commonly available. Vectors employing, for example, the 2$\mu$ origin of replication of Broach, J. R., *Meth Enz* (1983) 101: 307, or other yeast compatible origins of replications (see, for example, Stinchcomb, et al, *Nature* (1979) 282: 39, Tschempe, et al, *Gene* (1980) 10: 157 and Clarke, L, et al, *Meth Enz* (1983) 101: 300) may be used. Control sequences for yeast vectors include promoters for the synthesis of glycolytic enzymes (Hess, et al, *J Adv Enzyme Reg* (1968) 7: 149; Holland, et al, *Biochemistry* (1978) 17: 4900). Additional promoters known in the art include the promoter for 3-phosphoglycerate kinase (Hitzeman, et al, *J Biol Chem* (1980) 255: 2073), and those for other glycolytic enzymes. Other promoters, which have the additional advantage of transcription controlled by growth conditions are the promoter regions for alcohol dehydrogenase 2, isocytochrome C, acid phosphatase, degradative enzymes associated with nitrogen metabolism, and enzymes responsible for maltose and galactose utilization. It is also believed terminator sequences are desirable at the 3' end of the coding sequences. Such terminators are found in the 3' untranslated region following the coding sequences in yeast-derived genes.

It is also, of course, possible to express genes encoding polypeptides in eucaryotic host cell cultures derived from multicellular organisms. See, for example, *Tissue Cultures,* Academic Press, Cruz and Patterson, editors (1973). These systems have the additional advantage of the ability to splice out introns and thus can be used directly to express genomic fragments. Useful host cell lines include VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV 40) (Fiers, et al, *Nature* (1978) 273: 113), or other viral promoters such as those derived from polyoma, Adenovirus 2, bovine papiloma virus, or avian sarcoma viruses. The controllable promoter, hMTII (Karin, M., et al, *Nature* (1982) 299: 797–802) may also be used. General aspects of mammalian cell host system transformations have been described by Axel; U.S. Pat. No. 4,399,216 issued Aug. 16, 1983. It now appears, also that "enhancer" regions are important in optimizing expression; these are, generally, sequences found upstream or downstream of the promoter region in non-coding DNA regions. Origins of replication may be obtained, if needed, from viral sources. However, integration into the chromosome is a common mechanism for DNA replication in eucaryotes.

C.2. Transformations

Depending on the host cell used, transformation is done using standard techniques appropriate to such cells. The calcium treatment employing calcium chloride, as described by Cohen, S. N., *Proc Natl Acad Sci* (*USA*) (1972) 69: 2110, or the $RbCl_2$ method described in Maniatis, et al, *Molecular Cloning: A Laboratory Manual* (1982) Cold Spring Harbor Press, p. 254 may be used for procaryotes or other cells which contain substantial cell wall barriers. For mammalian cells without such cell walls, the calcium phosphate precipitation method of Graham and van der Eb, *Virology* (1978) 52: 546, optionally as modified by Wigler, M., et al, *Cell* (1979) 16: 777–785 may be used. Transformations into yeast may be carried out according to the method of Van Solingen, P., et al, *J Bact* (1977) 130: 946 or of Hsiao, C. L., et al, *Proc Natl Acad Sci* (*USA*) (1979) 76: 3829.

C.3. Probing cDNA or Genomic Libraries cDNA or genomic libraries are screened using the colony hybridization procedure. Each microtiter plate is replicated onto duplicate nitrocellulose filter papers (S & S type BA-85) and colonies are allowed to grow at 37° C. for 14–16 hr on L agar containing 15 $\mu$g/ml tetracycline. The colonies are lysed with 10% SDS and the DNA is fixed to the filter by sequential treatment for 5 min with 500 mM NaOH/1.5 NaCl, then 0.5M Tris HCl(pH 8.0)/1.5M NaCl followed by 2×standard sa- Synthetic oligonucleotides are prepared by the method of Efimov, V. A., et al (*Nucleic Acids Res* (1982) 6875-6894), and can be prepared using commercially available automated oligonucleotide synthesizers. Kinasing of single strands prior to annealing or for labeling is achieved using an excess, e.g., approximately 10 units of polynucleotide kinase to 1 nmole substrate in the presence of 50 mM Tris, pH 7.6, 10 mM $MgCl_2$, 5 mM dithiothreitol, 1-2 mM ATP, 1.7 pmoles $\gamma32P$-ATP (2.9 mCi/mmole), 0.1 mM spermidine, 0.1 mM EDTA.

Ligations are performed in 15-50 $\mu$l volumes under the following standard conditions and temperatures: 20 mM Tris-Cl pH 7.5, 10 mM $MgCl_2$, 10 mM DTT, 33 $\mu$g/ml BSA, 10 mM-50 mM NaCl, and either 40 $\mu$M ATP, 0.01-0.02 (Weiss) units T4 DNA ligase at 0° C. (for "sticky end" ligation) or 1 mM ATP, 0.3-0.6 (Weiss) units T4 DNA ligase at 14° C. (for "blunt end" ligation). Intermolecular "sticky end" ligations are usually performed at 33-100 $\mu$g/ml total DNA concentrations (5-100 nM total end concentration). Intermolecular blunt end ligations (usually employing a 10-30 fold molar excess of linkers) are performed at 1 $\mu$M total ends concentration.

In vector construction employing "vector fragments", the vector fragment is commonly treated with bacterial alkaline phosphatase (BAP) or calf intestinal alkaline phosphatase (CIP) in order to remove the 5' phosphate and prevent religation of the vector. Digestions are conducted at pH 8 in approximately 150 mM Tris, in the presence of $Na^+$ and $Mg^{+2}$ using about 1 unit of BAP or CIP per $\mu$g of vector at 60° for about one hour. In order to recover the nucleic acid fragments, the preparation is extracted with phenol/chloroform and ethanol precipitated. Alternatively, religation can be prevented in vectors which have been double digested by additional restriction enzyme digestion of the unwanted fragments.

For portions of vectors derived from cDNA or genomic DNA which require sequence modifications, site specific primer directed mutagenesis is used. This is conducted using a primer synthetic oligonucleotide complementary to a single stranded phage DNA to be mutagenized except for limited mismatching, representing the desired mutation. Briefly, the synthetic oligonucleotide is used as a primer to direct synthesis of a strand complementary to the phage, and the resulting double-stranded DNA is transformed into a phage-supporting host bacterium. Cultures of the transformed bacteria are plated in top agar, permitting plaque formation from single cells which harbor the phage.

Theoretically, 50% of the new plaques will contain the phage having, as a single strand, the mutated form; 50% will have the original sequence. The resulting plaques are hybridized with kinased synthetic primer at a temperature which permits hybridization of an exact match, but at which the mismatches with the original strand are sufficient to prevent hybridization. Plaques which hybridize with the probe are then picked, cultured, and the DNA recovered. Details of site specific mutation procedures are described below in specific examples.

C.6. Verification of Construction

In the constructions set forth below, correct ligations for plasmid construction are confirmed by first transforming *E. coli* strain MC1061 obtained from Dr. M. Casadaban (Casadaban, M., et al, *J Mol Biol* (1980) 138: 179-207) or other suitable host with the ligation mixture. Successful transformants are selected by ampicillin, tetracycline or other antibiotic resistance or using other markers depending on the mode of plasmid construction, as is understood in the art. Plasmids from the transformants are then prepared according to the method of Clewell, D. B., et al, *Proc Natl Acad Sci (USA)* (1969) 62: 1159, optionally following chloramphenicol amplification (Clewell, D. B., *J Bacteriol* (1972) 110: 667). The isolated DNA is analyzed by restriction and/or sequenced by the dideoxy method of Sanger, F., et al, *Proc Natl Acad Sci (USA)* (1977) 74: 5463 as further described by Messing, et al, *Nucleic Acids Res* (1981) 9: 309, or by the method of Maxam, et al, *Methods in Enzymology* (1980) 65: 499.

C.6. Hosts Exemplified

Host strains used in cloning and expression herein are as follows:

For cloning and sequencing, and for expression of construction under control of most bacterial promoters, *E. coli* strain MC1061 was used.

For M13 phage recombinants, *E. coli* strains susceptible to phage infection, such as *E. coli* strain JM101 are employed.

The cells used for expression are Chinese hamster ovary (CHO) cells.

D. Cloning and Expression of Human ASP

Canine ASP cDNA was used to provide suitable probes for the human ASP genomic and cDNA library. Thus, preliminary preparation of the canine form of the protein and of its coding sequences are described in ¶s D.1-D.4 below.

D.1. Purification of Canine ASP

Lung surfactant complex was prepared from canine lungs obtained from exsanguinated canines. All procedures, including the lavage, were performed at 4° C. and the isolated material was stored at −15° C.

The lungs were degassed and lavaged 3 times with one liter per lavage of 5 mM Tris-HCl, 100 mM NaCl, pH 7.4 buffer. The $Ca^{+2}$ concentration of this buffer was less than $5\times10^{-6}M$ (Radiometer F2112 Ca; Radiometer A/S, Copenhagen, Denmark). The pooled lung washings were spun at $150\times g_{av}$ for 15 min (Sorval RC2-B) to remove cellular material. The supernatant was then spun at $20,000\times g_{av}$ for 15 hr (Beckman L3-40) using a type 15 rotor (Beckman Instruments), and the resulting pellet was dispersed in buffer containing 1.64M sodium bromide. After equilibration for 1 hr, the suspension was spun at $100,000\times g_{av}$ for 4 hr (Beckman L5-50B) in a SW28 rotor (Beckman Instruments). The pellicle was resuspended in buffer and spun at $100,000\times g_{av}$ for 1 hr (Beckman L5-50B). This pellet was resuspended in double distilled water.

D.1.a. Lipid Purification

Pellet resuspended in water at a concentration of 10-15 mg phospholipid/ml was injected into a 50-fold volume excess of n-butanol (Sigrist, H., et al, *Biochem Biophys Res Commun* (1977) 74: 178-184) and was stirred at room temperature for 1 hr. After centrifugation at $10,000\times g_{av}$ for 20 min (Sorval RC2-B), the supernatant was dried under vacuum at 40° C. and the lipids were extracted (Folch, J., et al, *J Biol Chem* (1957) 226: 497-509).

line citrate (SSC). Filters are air dried and baked at 80° C. for 2 hr.

For nick-translated probe, the duplicate filters are prehybridized at 42° C. for 16-18 hr with 10 ml per filter of DNA hybridization buffer (50% formamide (40% formamide if reduced stringency), 5×SSC, pH 7.0, 5× Denhardt's solution (polyvinylpyrrolidine, plus Ficoll and bovine serum albumin; 1×=0.02% of each). 50 mM sodium phsophate buffer at pH 7.0, 0.2% SDS, 50 μg/ml yeast tRNA, and 50 μg/ml denatured and sheared salmon sperm DNA).

Samples are hybridized with nick-translated DNA probes at 42° C. for 12-36 hr for homologous species and 37° C. for heterologous species contained in 5 ml of this same DNA hybridization buffer. The filters are washed two times for 30 min, each time at 50° C., in 0.2×SSC, 0.1% SDS for homologous species hybridization, and at 50° C. in 3×SSC, 0.1% SDS for heterologous species hybridization. Filters are air dried and autoradiographed for 1-3 days at 31 70° C.

For synthetic (15-30 mer) oligonucleotide probes, the duplicate filters are prehybridized at 42° C. for 2-8 hr with 10 ml per filter of oligo-hybridization buffer (6×SSC, 0.1% SDS, 1 mM EDTA, 5× Denhardt's, 0.05% sodium pyrophosphate and 50 μg/ml denatured and sheared salmon sperm DNA).

The samples are hybridized with kinased oligonucleotide probes of 15-30 nucleotides under conditions which depend on the composition of the oligonucleotide. Typical conditions employ a temperature of 30°-42° C. for 24-36 hr with 5 ml/filter of this same oligo-hybridization buffer containing probe. The filters are washed two times for 15 min at 23° C., each time with 6×SSC, 0.1% SDS and 50 mM sodium phosphate buffer at pH 7, then are washed once for 2 min at the calculated hybridization temperature with 6×SSC and 0.1% SDS, air dried, and are autoradiographed at −70° C. for 2 to 3 days.

C.4. cDNA Library Production

Double-stranded cDNA is synthesized and prepared for insertion into the plasmid vector pBR322 using homopolymeric tailing mediated by calf thymus terminal transferase (Sutcliffe, J. G., *Nucleic Acid Res* (1978) 5: 2721-2732). First strand cDNA is synthesized by the RNA-dependent DNA polymerase from Avian Myeloblastosis Virus, by priming with oligo (dT) 12-18 on 5 μg mRNA. The RNA template is then liberated from the nascent DNA strand by denaturation at 100° C. for 5 min, followed by chilling on ice. Second strand DNA is synthesized by using the large fragment of DNA polymerase I of *E. coli*, relying on self-priming at the 3'-end of the first strand molecule, thereby forming a double-stranded hairpin DNA. These molecules are blunt-ended at the open-ended termini, and the hairpin loop is cleaved open with S1 nuclease from *Aspergillus oryzae*. S1 nuclease digestion of the double-stranded cDNA takes place in 300 mM NaCl, 30 mM NaOAc, pH 4.5, 3 mM $ZnCl_2$ for 30 min at 37° C. with 600 units enzyme. The cDNA is extracted with phenol:-chloroform, and small oligonucleotides are removed by three ethanol precipitations in the presence of ammonium acetate. This is done as follows: a half volume of 7.5M ammonium acetate and two volumes ethanol are added to the cDNA solution, which is precipitated at −70° C. The blunt-ended, double-stranded cDNA is then fractionated by size using gel filtration through a column (0.3×14 cm) Sepharose 4B (Pharmacia Fine Chemicals, Piscataway, NJ) or by ultracentrifugation in 5-20% glycerol gradient followed by fractionation of the gradient. cDNA roughly greater than the desired length, e.g., 300 base pairs is retained and recovered by precipitation with 70% ethanol. Short (10-30 nucleotides) polymeric tails of deoxycytosine are added to the 3' termini of the cDNA using a reaction containing 0.2M potassium cacodylate, 25 mM Tris, pH 6.9, 2 mM dithiothreitol, 0.5 mM $CoCl_2$, 200 mM cDTP, 400 μg/ml BSA, and 40 units calf thymus terminal deoxynucleotide transferase for 5 min at 22° C. The reaction is extracted with phenol:chloroform, and small oligonucleotides are removed with three ethanol precipitations in the presence of ammonium acetate.

The dC-tailed cDNA is annealed with pBR322 which has been cleaved with PstI and tailed with oligo dG: 2.5 μg pBR322-dG DNA is annealed with the cDNA at a vector concentration of 5 μg/ml, and the hybrids are transferred into *E. coli* MC1061 by the $CaCl_2$-treatment described by Casabadan, M., et al, *Mol Biol* (1980) 138: 179-207.

C.5. Vector Construction

Construction of suitable vectors containing the desired coding and control sequences employs standard ligation and restriction techniques which are well understood in the art. Isolated plasmids, DNA sequences, or synthesized oligonucleotides are cleaved, tailored, and religated in the form desired.

Site specific DNA cleavage is performed by treating with the suitable restriction enzyme (or enzymes) under conditions which are generally understood in the art, and the particulars of which are specified by the manufacturer of these commercially available restriction enzymes. See, e.g., New England Biolabs, Product Catalog. In general, about 1 μg of plasmid or DNA sequence is cleaved by one unit of enzyme in about 20 μl of buffer solution; in the examples herein, typically, an excess of restriction enzyme is used to insure complete digestion of the DNA substrate. Incubation times of about one hour to two hours at about 37° C. are workable, although variations can be tolerated. After each incubation, protein is removed by extraction with phenol/chloroform, and may be followed by ether extraction, and the nucleic acid recovered from aqueous fractions by precipitation with ethanol. If desired, size separation of the cleaved fragments may be performed by polyacylamide gel or agarose gel electrophoresis using standard techniques. A general description of size separations is found in *Methods in Enzymology* (1980) 65: 499-560.

Restriction cleaved fragments may be blunt ended by treating with the large fragment of *E. coli* DNA polymerase I (Klenow) in the presence of the four deoxynucleotide triphosphates (dNTPs) using incubation times of about 15 to 25 min at 20° to 25° C. in 50 mM Tris pH 7.6, 50 mM NaCl, 6 mM $MgCl_2$, 6 mM DTT and 5-10 μM dNTPs. The Klenow fragment fills in at 5' sticky ends but chews back protruding 3' single strands, even though the four dNTPs are present. If desired, selective repair can be performed by supplying only one of the, or selected, dNTPs within the limitations dictated by the nature of the sticky ends. After treatment with Klenow, the mixture is extracted with phenol/chloroform and ethanol precipitated. Treatment under appropriate conditions with S1 nuclease or Bal-31 results in hydrolysis of any single-stranded portion.

D.1.b. Protein Fractionation and Verification as ASP

The precipitate from the n-butanol extraction was dried under nitrogen and washed twice in 20 ml of buffer containing 20 mM octyl-$\beta$-D-glucopyranoside. After centrifugation at $100,000 \times g_{av}$ for 1 hr (Beckman L5-50B), the pellet was dispersed in 0.3M lithium diiodosalicylate, 0.05M, pyridine (pH 8.4) on ice, diluted with an equal volume of water, and mixed with a volume of n-butanol equal to the aqueous phase. A total of 9 n-butanol-water partitions were performed to lower the detergent concentration in the aqueous phase. The final lower, aqueous phase containing the protein was lyophilized for 15 hr, taken up in 2 ml of buffer and spun at $100,000 \times g_{av}$ (Beckman L5-50B) to remove any remaining insoluble material. The lithium diiodosalicylate concentration in the final sample, calculated from an extinction coefficient of $4 \times 10^3$ at 323 nm (Marchesi, V. T. and Andrews, E. P., *Science* (1971) 174: 1247–1248), was less than 10 $\mu$M.

The thus purified canine ASP 32K apoprotein was reconstituted with purified surfactant lipids of ¶ D.1.a. The reconstituted material had surface activity as measured by the surface balance and its in vivo biological activity was demonstrated by inspiration into fetal rabbits maintained on a ventilator.

D.1.c. Further Protein Purification

The protein fraction obtained in the previous subparagraph was reduced in incubation with 50 mM DTT in 1% SDS, 50 mM Tris-HCl, 1 mM EDTA pH 7.5 at 37° C. for 1 hr, alkylated with 100 mM iodoacetamide (Sigma) at 0° C. for 30 min, and subjected to polyacrylamide gel eletrophoresis by the procedure of Laemmli, U. K., *Nature* (1970) 227: 680–685. The proteins were visualized by soaking the gel in 4M sodium acetate solution and the 32K band was sliced out with a razor blade, and electroluted by the protocol of Hunkapiller, M. W., et al, *Methods in Enzymology* (1983) 91: 227–235, New York, Academic Press, using the CBS Scientific (Del Mar, Calif.) electrolution device.

The eluted protein was lyophilized and its N-terminal amino acid sequence was determined from one nanomole of protein using the Applied Biosystems 470A gas-phase sequencer (Applied Biosystems Inc., Foster City, CA) in accordance with the instructions of the manufacturer. PTH amino acids were identified with a Beckman 334T HPLC, using a $0.46 \times 25$ cm IBM CN-column. The gradient applied was as indicated in Hunkapiller, N. W., and Hood, L. E., *Methods in Enzymology* (1983) 91: 486–492, New York, Academic Press, with the following modifications: Instead of a binary gradient system a ternary gradient system was used in which acetonitrile and methanol were pumped by separate pumps and the ratio of the two varied with time over the course of the gradient, with appropriate modification of the gradient program; instead of the Permaphase ETH$^r$ guard column, a "$5 \times 0.46$ cm IBM CN" analytical "mini-column", was used; and the column was heated to 28° C., rather than to 32° C.

The N-terminal amino acid sequence was:

```
1                    5                    10
Ile—Glu—Asn—Asn—Thr—Lys—Asp—Val—Cys—Val—

15                   20
—Gly—Asn—Hyp—Gly—Ile—Hyp—Gly—Thr—Hyp—Gly—

25
—Ser—His—Gly—Leu—Hyp—Gly—Arg—?—Gly—

30
—Arg—?—Gly—Val.
```

"Hyp" indicates the modified amino acid hydroxyproline.

This sequence shows extensive homology with the N-terminal portion of human ASP prepared from a patient suffering from alveolar proteinosis (a syndrome which results from the presence of excess surfactant in the lung). The ASP was prepared by a similar protocol and has the N-terminal sequence:

```
1                    5                    10
Glu—Val—Lys—Asp—Val—Cys—Val—Gly—Ser—Hyp—

15
—Gly—Ile—Hyp—Gly—Thr—Hyp—Gly
```

Amino acids 3–17 of the human sequence are precisely homologous, except for the serine at position 9, to amino aciids 6–20 of the canine sequence.

Amino acid composition data for the canine protein show a hydroxyproline content consistent with the hydroxylation of proline residues in the deduced sequence (see ¶ D.4) which appear in the collagen-like pattern Gly-X-Hyp. As this pattern is also shown in the human N-terminal sequence it is probable, by analogy to the canine data, that similary disposed prolines in the human sequence are hydroxylated.

D.2. Isolation of Canine Lung mRNA

Total RNA was isolated from an adult canine lung by the method of Chirgwin, J. M., et al, *Biochemistry* (1979) 18: 5294–5299. The lung tissue was first pulverized by grinding with a mortar and pestle in liquid $N_2$, and homogenized in a solution of 6M guanidine thiocyanate, 0.05M Tris-HCl, pH 7.0, 0.1 M-$\beta$-mercaptoethanol, 0.5% Sarcrosyl. This homogenate was made 2.0M in CsCl and layered over a 5.7M CsCl cushion in 0.01M ethylenediaminetetraacetic acid (EDTA) and 0.05M Tris-HCl, pH 9.0. The RNA was pelleted through this cushion by centrifugation at $115,000 \times g$ for 16 hr, thereby separating it from the cellular DNA and protein which do not sediment through the higher density CsCl solution. The RNA was then dissolved in 0.01M Tris-HCl, pH 7.4, 0.005M EDTA, 1.0% sodium dodecylsulfate (SDS), extracted with a 1:1 mixture of chloroform and phenol, and precipitated from 70% ethanol. The polyadenylated RNA (poly A+ RNA) fraction was obtained by affinity chromatography through oligo (dT) cellulose as described by Aviv, H., and Leder, P., *Proc Natl Acad Sci* (USA) (1972) 69: 1840–1412.

D.3. Construction and Screening of Canine Lung cDNA Library

Adult canine lung poly A+ RNA prepared as in ¶ D.2 was used to construct a cDNA library as described in ¶ C.4, 5 $\mu$g mRNA yielded about 25 ng of cDNA, size-selected to greater than 300 base pairs. The library contained about 200,000 independent recombinants. Of these, 40,000 recombinants were plated on nitrocellulose filters. These filters served as the masters for subsequent replicas (in accordance with the method of Hanahan, D., and Meselson, M., *Gene* (1980) 10: 63–75.

D.3.a. Probes

Three probes were constructed: a mixture of 24×14-mer sequences complementary to the amino acids 1-5 having the sequence

(probe a); 64×14-mers complementary to the amino acids 7-11 having the sequence

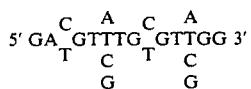

(probe b); and a single 15-mer

selected on the basis of mammalian codon preference (probe c). Each oligonucleotide mixture and the single unique oligonucleotide were synthesized on a Biosearch SAM I oligonucleotide synthesizer (Biosearch, Inc., San Rafael, CA) by a modification of the standard phosphotriester method using mesitylenesulfonyl chloride in the presence of N-methylimidazole as condensing reagents as described by Efimov, V. A., et al, *Nucleic Acids Res* (1982) 10: 6875-6894, and purified by polyacrylamide gel electrophoresis.

D.3.b. Probe Hybridization

Six replica filters were prepared from each master filter, so that each colony could be screened in duplicate with each of three oligonucleotide probes. Colonies recovered after replication off the master filters were placed on agar plates containing 170 μ/ml chloramphenicol for 18 hr. The colonies were then prepared for hybridization according to the method of Grunstein, M., and Hogness, D., *Proc Natl Acad Sci* (1975) 72: 3961-3972.

The filters were baked for 2 hr at 80° C. under vacuum and then washed for 4 hr at 68° C. with shaking in a large volume of 3×SSC (where 1×SSC is 0.15M NaCl, 0.015M sodium citrate, pH 7.5), 0.1% SDS. The filters were prehybridized in 6×SSC, 0.1% SDS, 1 mM EDTA, 5× Denhardt's solution (0.1% Ficoll, 0.1% polyvinylpyrrolidone, 0.1% bovine serum albumin) 0.05% sodium pyrophosphate and 50 μg/ml denatured salmon sperm DNA at 42° C. for a minimum of 2 hr.

Duplicate filters were then hybridized with 5×10⁶ cpm of one of each $^{32}$P-labeled oligonucleotide probe (phosphorylated in accordance with Maniatis, T., et al, *Molecular Cloning,* (1982) Cold Spring Harbor Laboratories, pp. 122-123) per filter in 10 ml hybridization solution containing identical ingredients as the prehybridization solution. Filters with oligonucleotide probes a, b, and c were hybridized at 37° C., 45° C., and 41° C., respectively. After 1 hr the thermostat was lowered to 28° C. for probe a and 37° C. for probe b, after which the bath was allowed to equilibrate. Filters with probe c were not hybridized at a lower temperature. The filters were washed twice in 6×SSC, 0.1% SDS at room temperature for 15 min, then washed in 6×SSC, 0.1% SDS at 37° C., 45° C., and 41° C. for probes a, b, and c, respectively, for 2 min. The final washing temperature was obtained form the empirical formula of Suggs, S. V., et al, *Developmental Biology Using Purified Genes* (ed. D. D. Brown and C. F. Fox), Academic Press, NY, pp. 683-693; that is, $T_d=4(G+C)+2(A+T)$. The hybridized filters were then dried and autoradiographed on Kodak ® XAR film with Dupont ® Cronex intensifying screens until complete exposures were obtained.

A colony was considered positive if it hybridized in duplicate with all three oligonucleotide probes or with both probes a and b. Of several potential positive clones, one hybridized much more intensely with probes a and b as compared to the others. Sequencing of this clone demonstrated that it encoded canine ASP and was designated DS-1.

D.4. Sequence of the Canine ASP cDNA

The purified DNA insert of 375 base pairs was excised from pDS-1 by restriction with PstI and prepared using small miniprep methods (Maniatis, et al, supra at p. 366) and was isolated on agarose gels. The intact DNA insert was then subcloned into bacteriophage M13 (Messing, J., and Vieira, J., *Gene* (1982) 19: 259-268) and sequenced using the dideoxy method of Sanger, F., et al, *Proc Natl Acad Sci* (USA) (1977) 74: 5463-5469. The sequence encoded the N-terminal portion of the approximately 300 amino acid protein, i.e., the 32 residue N-terminal amino acid sequence determined from the purified canine ASP of ¶ D.1, and 101 additional downstream amino acids. It also contained 50 base pairs of the 5' untranslated region.

The mRNA pool was assessed to determine the presence of sequences of sufficient length to encode the entire canine ASP sequence by Northern blot. Poly A+ RNA of ¶ D.2 was subjected to Northern blot using nick translated DS-1 insert DNA after fractionation by electrophoresis on a 1.4% agarose gel containing methylmercuric hydroxide by the method of Bailey, J. M. and Davidson, N., *Anal Biochem* (1976) 70: 75-85. mRNA hybridizing to probe was 1800-2000 nucleotides in length, clearly larger than the approximately 700 nucleotides needed for the coding sequence.

The DS-1 insert probe was therefore used to rescreen one duplicate set of original filters, which had been treated at 100° C. for 10 min to remove residual oligonucleotide probe. Filters were prehybridized in 0.75M NaCl, 0.075M Na citrate, 50% formamide, 0.5% SDS, 0.02% bovine serum albumin, 0.02% Ficoll-400,000, 0.02% polyvinyl pyrollidone, 0.1% sodium pyrophosphate, 50 μg.ml yeast tRNA and 50 μg/ml denatured sheared salmon sperm DNA) at 42° C. for 18 hr. 5×10⁵ cpm of $^{32}$P-labeled boiled DS-1 cDNA was added per ml fresh hybridization buffer and the filters were incubated in this buffer at 42° C. for 16 hr. They were then washed in 0.03M NaCl and 0.003M sodium citrate and 0.1% SDS two times each for 30 min at 50° C., and exposed for autoradiography overnight. Two additional clones, DS-4 and DS-31, were identified, which, together with DS-1, comprise roughly 1700 base pairs (FIG. 1).

DS-4 and DS-31 were also excised using PstI, subcloned in the PstI site of M13mp9, and sequenced by dideoxy sequencing according to the procedure of Sanger, F. (supra). The entire sequence contains two internal PstI sites. Confirmation of correct sequencing was obtained by dideoxy sequencing of fragments obtained from deduced internal restriction sites, as shown in FIG. 1. The entire nucleotide sequence including the amino acid sequence of ASP deduced from the 256 codon open reading frame is shown in FIG. 1.

Further confirmation of the deduced sequence and information regarding processing was obtained by purification and sequencing of collagenase treated canine ASP.

Purified canine ASP was digested with bacterial collagenase (Worthington, Freehold NJ) at a 1:1 enzyme:substrate ratio in 5 mM Tris pH 7.4–5 mM $CaCl_2$ at 37° C. That produced a 22 kD limit digest product as analyzed on SDS gels. This 22 kD band was electroeluted from a gel and subjected to amino acid sequence analysis as described above (¶ D.1.c). Two amino acids were identified at each cycle, indicating that the collagenase treatment had produced two peptides which remain linked by a disulfide bridge. From the cDNA clone sequence it can be demonstrated that the two sequences correspond to amino acids 78–110 and 203–232 in the intact molecule. The sequences obtained are:

```
          2      4      6       8      10
       Gly—Pro—Hyp—Gly—Leu—Pro—Ala—Ser—Leu—Asp—Glu—
       Gly—Lys—Glu—Gln—Cys—Val—Glu—Met—Tyr—Thr—Asp—

12      14      16      18      20
       —Glu—Leu—Gln—Thr—Thr—Leu—His—Asp—Leu—Arg—
       —Gly—Gln—Trp—Asn—Asn—Lys—Asn—Cys—Leu—Gln—

22      24      26      28
       —His—Gln— Ile —Leu—Gln—Thr—Met—Gly—
       —Tyr—Arg—Leu—Ala— Ile —Cys—Glu—Phe 30      32
                                 —Val—Leu—Ser—Leu
``` and demonstrate that the C-terminus of the molecule is not processed after translation.

D.5. Isolation of the human ASP Gene

A human genomic library cloned into bacteriophage Charon 28 (Rimm, D. L., et al, *Gene* (1980) 12: 301–310) was obtained from Dr. T. Maniatis, Harvard University. Approximately $1.5 \times 10^6$ phage were grown on *E. coli* K803, and plaque lysates were transferred to nitrocellulose filters as described by Benton, W. D., et al, *Science* (1977) 196: 180–182. The filters were probed with DS-1 cDNA which had been kinased by the nick-translation method of Rigby, P. W. J., et al, *J Mol Biol* (1977) 113: 237–251. Filters were prewashed in hybridization buffer (0.75M NaCl, 0.75M sodium nitrate, 40% formamide, 0.05% SDS, 0.02% bovine serum albumin, 0.02% Ficoll-400,000, 0.02% polyvinyl pyrollidone, 0.1% sodium pyrophosphate, 50 µg/ml yeast tRNA, 50 µg/ml denatured sheared salmon sperm DNA) at 42° C. for 1 hr. $5 \times 10^5$ cpm probe was added per ml fresh hybridization buffer and the filters were incubated in this buffer at 37° C. for 16 hr. They were then washed in 0.45M NaCl and 0.045M sodium citrate and 0.1% SDS two times at 50° C., and exposed for autoradiography overnight. Six potential clones containing sequences hybridizing to DS-1 cDNA were purified. The most strongly hybridizing clone, gHS-15, was characterized.

A 700 by EcoRI fragment from gHS-15 hybridized with the DS-1 probe and was chosen for sequence analysis. This EcoRI fragment was purified, inserted into M13mp9, sequenced and found to be extensively homologous with the corresponding canine sequence.

The entire human coding region was contained within two contiguous BamHI fragments: a 5' 1.2 kb and a 3' 3.5 kb fragment. Both BamHI fragments were individually subcloned into the BamHI site of M13mp8 and sequenced. Additional fragments were similarly sequenced according to the strategy shown in FIG. 2. The sequence information was analyzed using various Intelligenetics (Palo Alto, CA) computer programs in accordance with the instructions of the manufacturer. The regions containing the signal peptide, precursor sequence and mature apoprotein were identified by comparison to the canine ASP cDNA. From the sequence analysis, the 5' terminus of the gene is encoded within the 1.2 kb BamHI fragment and the 3' terminus within the 3.5 kb BamHI fragment. The gene is interrupted by three introns at positions 1218 bp, 1651 bp and 2482 bp, with position 1 being the first bp of the 1.2 BamHI fragment. The entire sequence, including the amino acid sequence of human ASP protein deduced is shwon in FIG. 3.

D.6. Expression of Human ASP

The phage isolate gHS-15 identified in ¶ D.5 as harboring an insert of approximately 16 kb containing the entire human ASP gene was transferred into CHO cells which had been grown in McCoy's medium with 10% fetal bovine serum by co-transformation with pSV2:NEO (Southern, P., et al, *J Mol Appl Genet* (1982) 1: 327–341), a plasmid containing a functional gene conferring resistance to the neomycin analog G148, which is toxic to mammalian cells. In the transformation, 15 µg of the λ:gHS-15 and 2 µg of pSV2:NEO were applied to a 100 mm dish of CHO cells in a calcium phosphate/DNA coprecipitate according to the method of Wigler, M., et al, *Cell* (1979) 16: 777–785, with inclusion of a 2 min "shock" with 15% glycerol 4 hr after exposure to the DNA. The cells were transferred to medium containing 1 µg/ml G418, and yielded about 50 stable transformants per 100 mm dish.

Stable transformants were cultured prior to labeling in media supplemented with 0.25 mM ascorbic acid. Two pools of stable transformants and one pool of untreated CHO cells were grown for 1 hr in medium containing 1/10 of normal methionine concentration and then labeled with $^{35}$S-methionine for 8–16 hours, and the $^{35}$S-met labeled total secreted proteins were analyzed by SDS-polyacrylamide gel electrophoresis. The results are shown in FIG. 6. Lane 1 shows the normal CHO secreted proteins. Lanes 2 and 3 display λ: gHS-15 secreted proteins: both of which have an additional 30–36 kD protein corresponding to an expressed ASP protein. To further document the identity of the 30–36 kD protein one can immunoprecipitate the total secreted protein samples with canine ASP antibodies. The vector λ:gHS-15 was deposited with the American Type Culture Collection on Dec. 7, 1984 and has accession no. ATCC 40146.

D.7. Construction of Additional Expression Vectors

Vectors suitable for expression of the genomic ASP encoding sequence in mammalian cells, which are capable of processing intron-containing DNA were constructed. Expression is controlled by the methallothionein II (hMTII) control sequences, as described by Karin, M., et al, *Nature* (1982) 299: 797–802.

The host vector, pMT is obtained by ligating the promoter into pUC8 as follows:

Plasmid 84H (Karin, M., et al (supra)) which carries the hMTII gene was digested to completion with BamHI, treated with exonuclease Bal-31 to remove terminal nucleotides, and then digested with HindIII to liberate an 840 bp fragment containing nucleotides −765 to +70 of the hMTII gene (nucleotide +1 is the first nucleotide transcribed). The 840 bp fragment was isolated and ligated with HindIII/HincII digested pUC8 (Vieria, J., et al, *Gene* (1982) 19: 259–268) and the ligation mixture transformed into *E. coli* MC1061. The correct construction of pMT was confirmed by dideoxy nucleotide sequencing.

In addition, a derivative of the pMT, pMT-Apo, containing C-terminal regulatory signals was prepared as shown in FIG. 4. pMT-Apo harbors a portion of the human liver protein ApoA$_1$ gene (Shoulders, C. C., et al, *Nucleic Acids Res* (1983) 11: 2827–2837) which contains the 3'-terminal regulatory signals. A PstI/PstI 2.2 kb fragment of ApoA$_1$ gene (blunt ended) was cloned into the SmaI site of the pMT polylinker region, and the majority of the ApoA$_1$ gene removed by digestion with BamHI, blunt ending with Klenow, digestion with StuI, and religation. The resulting vector contains roughly 500 bp of the ApoA$_1$ gene from the 3' terminus as confirmed by dideoxy-sequence analysis.

Five constructs of the human ASP gene and the pMT and pMT-Apo expression vectors were prepared using the 1.2 kb and 3.5 kb BamHI fragments of gHS-15. (See FIG. 4.) All constructs were isolated and confirmed by both restriction analysis and dideoxy sequencing. These constructs were prepared as follows:

1. the 1.2 kb and 3.5 kb BamHI fragments were cloned into the BamHI site of pMT to give pMT:gHS;
2. the 1.2 kb BamHI fragment was truncated at the 5' terminus by digestion with HinfI (position 950) and filled in with Klenow. The truncated fragment was cloned, along with the 3.5 kb fragment into the BamHI site of pMT to give pMT:gHS (HinfI);
3. the fragments of ¶ 2 were cloned instead into the BamHI site of pMT-Apo to give pMT-Apo:gHS (HinfI);
4. the 3.5 kb BamHI fragment was truncated at the 3' terminus by digestion with EcoRI (position 3434) and filled in with Klenow. This truncated fragment was cloned, along with the truncated 1.2 kb fragment truncated with HinfI as above into the BamHI site of pMT-Apo to give pMT-Apo:gHS (HinfI/EcoRI);
5. the 1.2 kb fragment was truncated at the BstEII site at position 356 and the 3.5 kb fragment at the BstEII site at position 4024. These fragments were cloned into the BamHI site of pMT-Apo to give pMT-Apo:gHS (BstEII).

The resulting pMT:gHS constructs were transferred into CHO cells as set forth in ¶ D.6 except that $10^{-4}$M ZnCl$_2$ was added with $^{35}$S-methionine to induce the metallothionein promoter and label the proteins produced.

After 8–16 hr the medium is analyzed for $^{35}$S-met labeled total secreted protein which immunoprecipitates with antibodies to canine ASP. Non-immune IgG are used as a control.

D.8. Preparation of a Human ASP cDNA Library

Human lung was obtained from two fetuses, one 22 weeks, the other 24 weeks of age. 7 g of lung tissue was first pulverized by grinding with a mortar and pestel in liquid N$_2$, and total poly A$^+$ RNA prepared as set forth in ¶ D.2 (supra).

A cDNA library was prepared from the mRNA as set forth in ¶ C.4. Five μg of lung poly A$^+$ RNA yielded about 25 ng of cDNA, size-selected to greater than 500 base pairs, and gave a library of 300,000 independent recombinants.

60,000 members of the human cDNA library were screened with the canine DS-1 cDNA in the manner described in ¶ D.5 for the screening of the genomic library. The recombinant colonies were plated on nitrocellulose filters which served as masters for two sets of replicas. The colony filters were then prepared for hybridization according to the method of Grunstein, M., and Hogness, D. (supra). The filters were baked for 2 hr at 80° C. under vacuum and then washed for 4 hr at 68° C. with shaking in a large volume of 3×SSC and 0.1% SDS. Next the filters were prehybridized in 0.75M NaCl, 0.075M sodium nitrate, 40% formamide, 0.5% SDS, 0.02% bovine serum albumin, 0.02% Ficoll-400,000, 0.02% polyvinyl pyrollidone, 50 μg/ml yeast tRNA, 50 μg/ml denatured sheared salmon sperm DNA) at 37° C. for 18 hr. One×$10^6$ cpm of $^{32}$P-labeled Ds-1 probe was added per ml of fresh hybridization buffer then incubated for 16 hr at 37° C. The filters were then washed in 0.45M NaCl and 0.045M sodium citrate and 0.01% SDS two times each for 30 min at 50° C., and exposed for autoradiography overnight.

One positively hybridizing clone, HS-6, was further analyzed by sequence determination; HS-6 harbors a 1.2 kb insert which can be released from the vector using PstI digestion, and which bears an internal EcoRI site. Both PstI-EcoRI fragments from the insert were subcloned into the PstI-EcoRI site of M13mp8 and mp9, and partial sequences obtained. The over 200 hp sequenced portion corresponds perfectly to the 3' end of gHS-15. The nucleotide sequence of HS-6 is shown in FIG. 5.

As the HS-6 cDNA insert contained only the 3'-terminal region of the ASP mRNA, the remaining clones were screened for adjacent surfactant sequences using HS-6 as probe. No clones were found in the remainder of the library.

To obtain complete human ASP cDNA, mRNA prepared from adult human lung by the procedure described in ¶ D.2 is used. Adult lung is greatly enriched in ASP transcripts as compared to fetal lung tissue (our observations) and therefore affords a greater frequency of obtaining a complete ASP cDNA.

Approximately 5 μg of adult lung mRNA is used to prepare double stranded, blunt end cDNA as described in ¶ C.4, but using a 17 nucleotide sequence derived from the 3'-untranslated region (beginning at 3450 bp) of HS-6 (5' GGGTGCCTCCAGTCCCA 3') as primer, which will permit only the synthesis of ASP cDNA. EcoRI linkers are then ligated to the blunt ended termini if the cDNA using T$_4$ ligase, the resultant digested with EcoRI and purified by agarose gel electrophoresis and elution. The cDNA is ligated to an appropriate vector such as pBR322 (previously digested with EcoRI and phosphatase treated) and transformed into competent bacteria such as *E. coli* MC1061. Recombinants are selected using agar plates containing the appropriate drug for the selected vector. Successful tranformants are replicted onto duplicate sets of nitrocellulose filters for hybridization.

The filters are baked for 2 hr at 80° C. under vacuum and then washed for 4 hr at 68° C. with shaking in a large volume of 3×SSC and 0.1% SDS. Next the filters are prehybridized in 0.75M NaCl, 0.075M sodium citrate, 50% formamide, 0.5% SDS, 0.02% bovine serum alumbin, 0.02% Ficoll-400,000 0.02% polyvinyl pyrollidone, 50 μg/ml yeast tRNA, 50 μg/ml denatured sheared salmon sperm DNA at 42° C. for 18 hr.

One×10⁶ cpm of ³²P-labeled HS-6 cDNA probe is added per ml of hybridization buffer and the filters incubated in this buffer for 16 hr at 42° C. The filters are then washed in 0.03M NaCl and 3 mM sodium citrate and 0.05% SDS two times each for 30 min at 50° C., and exposed for autoradiography overnight. Clones which hybridize to HS-6 probe are further characterized by restriction digestion with EcoRI. Those clones over 1 kb should contain the entire coding region of the human ASP protein and these clones can be sequenced to provide both identity and completeness.

We claim:

1. Human alveolar surfactant protein (ASP) in substantially pure form having the amino acid sequence encoded by the DNA shown in FIG. 3 as exon II-IV DNA and that portion of the exon I DNA encoding mature ASP amino acid sequence.

and by the naturally occurring allelic variants thereof, wherein the ASP is selected from the group consisting of the aforesaid directly encoded amino acid sequence, and said directly encoded amino acid sequence wherein at least one proline residue is substituted for by a hydroxypyroline residue, and wherein said ASP may be in glycosylated or unglycosylated form.

2. The ASP of claim 1 wherein at least three proline residues are substituted for by hydroxyproline residues.

3. The ASP of claim 2 wherein all proline residues are substituted for by hydroxyproline residues.

4. Canine alveolar surfactant protein (ASP) in substantially pure form having the amino acid sequence encoded by the DNA sequence shown as encoding mature ASP in FIG. 1 and by the naturally occurring allelic variants thereof, wherein as ASP is selected from the group consisting of the aforesaid directly encoded amino acid sequence and said directly encoded amino acid sequence wherein at least one proline residue is substituted for by a hydroxyproline, and wherein said ASP is in glycosylated or unglycosylated form.

5. The ASP of claim 4 wherein at least four hydroxyproline residues are substituted for by hydroxyproline.

6. The ASP of claim 5 wherein all proline residues are substituted for by hydroxyproline.

7. A pharmaceutical composition effective in treating respiratory distress syndrome (RDS) in mammals, which composition comprises the human ASP of claim 1 in admixture with a pharmaceutically acceptable excipient.

8. A method of treating respiratory distress syndrome in mammals which comprises administering to a subject mammal in need of such treatment an effective amount of human ASP of claim 1 or a pharmaceutical composition containing it.

9. A pharmaceutical composition comprising the human ASP of claim 1 in the form of a complex with natural or synthetic lipids.

10. The composition of claim 9 wherein the complex is comprised of between about 50% and almost 100% (wt/wt) lipid.

11. The composition of claim 10 wherein the complex contains approximately 80–95% lipid.

12. The composition of claim 9 wherein the lipid portion of the complex is approximately 80–90% dipalmitoyl phosphatidyl chlorine (DPPC).

13. The composition of claim 12 wherein the lipid portion of the complex also contains a unsaturated phosphatidyl choline, phosphatidyl glycerol, triacyl glycerol, palmitic acid, or mixtures thereof.

14. The composition of claim 9 which further includes at least one pharmaceutically acceptable excipient.

* * * * *